US007945077B2

(12) United States Patent
Demos (10) Patent No.: US 7,945,077 B2
(45) Date of Patent: May 17, 2011

(54) HYPERSPECTRAL MICROSCOPE FOR IN VIVO IMAGING OF MICROSTRUCTURES AND CELLS IN TISSUES

(75) Inventor: Stavros G. Demos, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 966 days.

(21) Appl. No.: 11/292,406

(22) Filed: Nov. 30, 2005

(65) Prior Publication Data

US 2007/0160279 A1  Jul. 12, 2007

(51) Int. Cl.
G06K 9/00 (2006.01)
(52) U.S. Cl. ........................................ 382/128; 600/473
(58) Field of Classification Search .................. 382/128; 600/473
See application file for complete search history.

(56) References Cited

U.S. PATENT DOCUMENTS

| | | | |
|---|---|---|---|
| 5,782,770 A | 7/1998 | Mooradian et al. | |
| 5,986,770 A | 11/1999 | Hein et al. | |
| 6,507,747 B1 | 1/2003 | Gowda et al. | |
| 6,529,769 B2 | 3/2003 | Zigler | |
| 7,149,567 B2 * | 12/2006 | Demos et al. | 600/473 |
| 2002/0049386 A1 | 4/2002 | Yang et al. | |
| 2002/0065468 A1 | 5/2002 | Utzinger et al. | |
| 2002/0103439 A1 | 8/2002 | Zeng et al. | |
| 2004/0006275 A1 * | 1/2004 | Demos et al. | 600/476 |
| 2005/0218338 A1 * | 10/2005 | Wulf et al. | 250/458.1 |
| 2008/0194969 A1 * | 8/2008 | Werahera et al. | 600/476 |

OTHER PUBLICATIONS

R. R. Alfano et al., "Laser induced fluorescence spectroscopy from native cancerous and normal tissues", by IEEE J. Quantum Electron., 20, 1507-1511 (1984).
C. R. Kapadia et al., "Laser-induced fluorescence spectroscopy of human colonic mucosa detection of adenomatous transformation", Gastroenterology, 99, 150-157 (1990).

(Continued)

Primary Examiner — John B Strege
(74) Attorney, Agent, or Firm — John P. Wooldridge (57) ABSTRACT

An optical hyperspectral/multimodal imaging method and apparatus is utilized to provide high signal sensitivity for implementation of various optical imaging approaches. Such a system utilizes long working distance microscope objectives so as to enable off-axis illumination of predetermined tissue thereby allowing for excitation at any optical wavelength, simplifies design, reduces required optical elements, significantly reduces spectral noise from the optical elements and allows for fast image acquisition enabling high quality imaging in-vivo. Such a technology provides a means of detecting disease at the single cell level such as cancer, precancer, ischemic, traumatic or other type of injury, infection, or other diseases or conditions causing alterations in cells and tissue micro structures.

31 Claims, 10 Drawing Sheets

OTHER PUBLICATIONS

R. R. Kortum et al., "Spectroscopic diagnosis of colonic dysphasia", Photochem & Photobio., 53, 777-786, (1991).

C. J. Frank et al., "Characterization of human breast specimens with Near-IR Raman spectroscopy", Anal. Chem., 66, 319-326 (1994).

I. Pavlova et al., "Microanatomical and biochemical origins of normal and precancerous cervical autofluorescence using laser-scanning fluorescence confocal microscopy", 77, 550-555 (2003).

Z.W. Huang et al., "Laser-induced autofluorescence microscopy of normal and tumor human colonic tissue", Int.J.I Of Oncology, 24, 59-63 (2004).

M. Rajadhyaksha et al., "Confocal examination of nonmelanoma cancers in thick skin excisions to potentially guide Mohs micrographic surgery without frozen histopathology", J. of Investigative Dermatology, 117, 1137-1143 (2001).

J. N. Gannaway et al., "Second harmonic imaging in the scanning optical microscope", Optical and Quantum Electronics, 10, 435-439(1978).

W. Denk et al., "Two-photon Laser scanning fluorescence microscopy", Science, 248. 73-76 (1990).

A. Zumbusch et al., "Three-dimensional vibrational imaging by coherent anti-Stokes Raman scattering", Phys. Rev. Lett., 82, 4142-4145 (1999).

N. Ramanujam et al., "Cervical precancer detection using a multivariate statistical algorithm based on laser-induced fluorescence spectra at multiple excitation wavelengths", Photochemistry and Photobiology, 64, 720-735 (1996).

V. Backman et al., "Detection of preinvasive cancer cells", Nature, 406, 35-36 (2000).

W. Hsing-Wen et al., "Quantitative laser scanning confocal autofluorescence microscopy of normal, premalignant, and malignant colonic tissues", IEEE Transactions on Biom. Engineering, 46, 101246-52 (1999).

* cited by examiner

HYPERSPECTRAL MICROSCOPE FOR IN VIVO IMAGING OF MICROSTRUCTURES AND CELLS IN TISSUES

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a medical diagnostic for investigating tissue components. More particularly, the present invention relates to a micro-scale instrument that utilizes autofluorescence emission and/or polarized elastic light scattering for real-time monitoring of microstructures and cells in tissues.

2. Description of Related Art

The diagnostic gold-standard of histological evaluation of living tissues typically entails fixation, sectioning, and staining to obtain thin samples which exhibit high contrast under the microscope. While this process has led to a much deeper understanding of cellular structure, tissue sectioning is time consuming, requires removal of tissue from the patient, and has inherent sampling error. However, the most important limitation is the delay, due to processing, in providing the surgeon with clinically relevant information at the time of surgery. While frozen section analysis is an accepted practice, this technique can be used only for readily identifiable lesions. Thus, there is clearly a need to develop new methods to complement existing modalities by providing the surgeon real time information that could be used intra-operatively to identify suspect lesions.

In recent years, technological developments in laser and detection instrumentation have facilitated the exploration of optical spectroscopic techniques for the detection and monitoring of disease at the tissue level. A number of spectroscopic approaches utilizing tissue autofluorescence and/or light scattering have led the way in the development of photonic methods for in-vivo characterization of tissue structures. Background information for such techniques can be found in: "Laser induced fluorescence spectroscopy from native cancerous and normal tissues", by R. R. Alfano, B. Tata, J. Cordero, P. Tomashefsky, F. W. Longo. M. A. Alfano IEEE J. Quantum Electron., 20, 1507-1511 (1984); "Laser-induced fluorescence spectroscopy of human colonic mucosa detection of adenomatous transformation", by C. R. Kapadia, F. W. Cutruzzola, K. M. O'Brien, M. L. Stetz, R. Enriquez, L. I. Deckelbaum, Gastroenterology, 99, 150-157 (1990); "Spectroscopic diagnosis of colonic dysphasia", by R. R. Kortum, R. P. Rava, R. E. Petras, M. Fitzmaurice, M. Sivak, M. S. Feld, Photochem & Photobio., 53, 777-786, (1991); "Characterization of human breast specimens with Near-IR Raman spectroscopy", by C. J. Frank, D. C. Redd, T. S. Gansler, R. L. McCreery, Anal. Chem., 66, 319-326 (1994); "Cervical precancer detection using a multivariate statistical algorithm based on laser-induced fluorescence spectra at multiple excitation wavelengths", by N. Ramanujam, M. F. Mitchell, A. MahadevanJansen, S. L. Thomsen, G. Staerkel, A. Malpica, T. Wright, N. Atkinson, R. Richards-Kortum, Photochemistry and Photobiology, 64, 720-735(1996); and "Detection of preinvasive cancer cells", by V. Backman, M. B. Wallace, L. T. Perelman, J. T. Arendt, R. Gurjar, M. G. Muller, Q. Zhang, G. Zonios, E. Kline, T. McGillican, S. Shapshay, T. Valdez, K. Badizadegan, J. M. Crawford, M. Fitzmaurice, S. Kabani, H. S. Levin, M. Seiler, R. R. Dasari, I. Itzkan, J. Van Dam, M. S. Feld, Nature, 406, 35-36 (2000).

Although these techniques have been explored extensively at the macroscopic level for more than a decade, their recent adaptation to the microscopic level has demonstrated their capability to image tissue micro-structures directly correlated to the histopathology of the tissue. Using confocal microscopy, tissue imaging at the microscopic level has been demonstrated using autofluorescence and light scattering. Background information on such methods and instrumentation can be found in: "Quantitative laser scanning confocal autofluorescence microscopy of normal, premalignant, and malignant colonic tissues", by W. Hsing-Wen, J. Willis, M. J. F. Canto, M. V. Jr. Sivak, J. A. Izatt, IEEE Transactions on Biom. Engineering, 46, 101246-52 (1999); "Microanatomical and biochemical origins of normal and precancerous cervical autofluorescence using laser-scanning fluorescence confocal microscopy", by I. Pavlova, K. Sokolov, R. Drezek, A. Malpica, M. Follen, R. Richards-Kortum, Photochem Photobiol., 77, 550-555 (2003); "Laser-induced autofluorescence microscopy of normal and tumor human colonic tissue", by Z. W. Huang, W. Zheng, S. S. Xie, R. Chen, H. S. Zeng, D. I. McLean, H. Lui, Int. J. 1 Of Oncology, 24, 59-63 (2004); "In vivo, real-time confocal imaging", by J. V. Jester, P. M. Andrews, W. M. Petroll, M. A. Lemp, H. D. Cavanagh, J Electron Microsc Tech. 18, 50-60, (1991), and "Confocal examination of nonmelanoma cancers in thick skin excisions to potentially guide Mohs micrographic surgery without frozen histopathology", by M. Rajadhyaksha, G. Menaker, T. Flotte, P. J. Dwyer, S. Gonzalez., J. of Investigative Dermatology, 117, 1137-1143 (2001).

The development of ultrafast lasers stimulated the utilization of nonlinear interactions of ultrashort pulses with cell components. Second harmonic generation imaging arises only by molecules which are noncentrosymmetric, and hence contrast is a function of the molecular structure of the specimen and its orientation with respect to the laser beam. Two-photon laser scanning microscopy offers higher resolution than confocal microscopy using infrared pulses for excitation. Coherent anti-Stokes Raman scattering microscopy offers the possibility for imaging by targeting specific molecular species. Background information on such nonlinear imaging techniques can be found in: "Second harmonic imaging in the scanning optical microscope" by J. N. Gannaway, C. J. R. Sheppard, Optical and Quantum Electronics, 10, 435-439 (1978); "Two-photon Laser scanning fluorescence microscopy" by W. Denk, J. H. Strickler, W. W. Webb, Science, 248, 73-76 (1990); and "Three-dimensional vibrational imaging by coherent anti-Stokes Raman scattering" by A. Zumbusch, G. R. Holtom, and X. S. Xie, Phys. Rev. Lett., 82, 4142-4145 (1999).

These nonlinear imaging techniques offer unique diagnostic capabilities, however their implementation in a clinical environment requires the accommodation of complex instrumentation and specialized technical expertise. On the other hand, confocal microscopy is less complex but the light collection efficiency is only a small fraction of that of conventional fluorescence microscopy. In addition, the focused beam used in confocal microscopy leads to even less efficient autofluorescence signal collection due to photo-bleaching of native tissue fluorophores and sets a limitation on the excitation energy permissible thus increasing the necessary integration times. Furthermore, it is very difficult to incorporate hyperspectral imaging techniques in a confocal microscope without major compromises in the instrument's size and cost. Although these issues may be easily resolvable for some applications, the in-vivo application of these advanced microscopies in a clinical setting may be proven challenging.

Accordingly, a need exists for a microscopy system and method that incorporates hyperspectral/multimodal imaging while offering high spatial resolution and optimized signal sensitivity for fast image acquisition. The present invention is directed to such a need.

SUMMARY OF THE INVENTION

Accordingly, the present invention is directed to a high resolution optical imaging method, that includes: illuminating at one or more incidence angles, one or more structures and cells of tissue components using one or more predetermined off-axis illumination sources; microscopically interrogating the illuminated structures and cells using one or more optical elements, wherein the optical elements further include long working distance objectives; collecting one or more spectral bands and/or a degree of polarization states resulting from the interrogation; and processing the collected one or more spectral bands and/or polarization states resulting from the one or more incidence illumination angles to enhance image contrast and visibility of the interrogated structures and cells.

Still another aspect of the present invention is directed to an optical apparatus that can provide high signal sensitivity while utilizing various optical imaging approaches. Such a system utilizes long working distance microscope objectives so as to enable off-axis illumination of predetermined tissue thereby allowing for excitation at any optical wavelength and so as to substantially eliminate spectral noise from the optical elements.

Accordingly, the present provides hyperspectral imaging methods and a simple less expensive microscope apparatus that enables real-time monitoring of microstructures and cells in tissues having high signal sensitivities and a spatial resolution of down to about 0.5 µm. Such a system, as disclosed herein, utilizes excitation of wavelengths greater than about 200 nm and off-axis illumination so as to substantially eliminate spectral noise from arranged optical elements.

Applications of the imaging instrument of the present invention include delineating a tumor's margins, screening of small tumors not visible in the macroscopic field, and monitoring of tissues or organs during treatment or exposure to adverse conditions (e.g., change of tissue chromophore properties, location of uptake of contrast agent, cell swelling etc.). Additional applications include, but are not limited to, biosecurity, basic and applied research in Biology, injury ischemia recovery, dental tissue analysis, cosmetic applications (e.g., nails, pigmentation or disease visualization), the detection and diagnosis of diseases (e.g., cancer), and the rapid pathological assessment and the capability of providing surgical guidance (e.g., civilian and battlefield trauma scenarios). Moreover, the present invention also provides for simpler and lower cost instrumentation, with increased signal sensitivity allowing for fast image acquisition suitable for in vivo applications in a human (e.g., endoscopic microscopy applications) or monitoring of other processes that require fast image acquisition.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring now to the drawings, specific embodiments of the invention are shown. The detailed description of the specific embodiments, together with the general description of the invention, serves to explain the principles of the invention.

General Description

A real-time monitoring microscope system of the present invention (suitable for in vivo application in a clinical setting) provides: a) contrast between components of intact tissue with no processing to reveal histopathologic information, b) sufficiently high spatial resolution of down to about 0.5 µm to separate structures and components of interest and, c) fast image acquisition by utilizing pulsed sources for real time imaging of an object (tissue component or organ) that may be continuously moving due to heartbeat and blood flow.

The main strength of the microscope of the present invention for interrogation of microstructures and cells in tissues is the combined investigative hyperspectral/multimodal imaging approach (i.e., the use of various spectroscopic techniques and multiple wavelength and/or spectral bands) utilizing polarized light scattering with autofluorescence and/or fluorescence under predetermined white light and/or laser excitation.

The present invention can be arranged as a portable endoscopic system for clinical use or more often as a simple and inexpensive portable table-top microscope that can differentiate various cellular components and microstructures (e.g., to identify tumors, to evaluate dental tissue, to provide cosmetic evaluation (pigmentation or disease visualization)) by keying on "signature" optical characteristics, such as, tissue-specific polarized or unpolarized light scattering and/or endogenous autofluorescence that includes NIR autofluorescence and/or fluorescence produced by exogenous furnished fluorophores (i.e., via contrast agents). Such "signature" optical characteristics are induced in interrogated tissue components by directed white light illumination and/or broadband or substantially illumination wavelengths of greater than about 200 nm, often by pulsed coherent excitation of less than about 10 µsec in duration and imaged without having to make any modification to the instrumentation of the microscope other than to change predetermined wavelengths and/or predetermined optical components, such as, for example, bandpass and/or polarization filters located in front of a predetermined detector.

The detector configured within the present invention is designed to acquire the various imaging modalities (e.g., desired fluorescence, autofluorescence and/or scattered spectra of polarized and/or unpolarized light images) and a processor compares such imaging modalities and/or is manipulated to perform inter-image operations to provide contrast so as to identify and assess native tissue chromophores and/or exogenous fluorophores at the cellular and subcellular level in an expedient manner.

As additional benefits, identified structures (e.g. cells and microstructures) by the presence of highlighting the spatial distribution of tissue chromophores and/or exogenous fluorophores, using techniques and apparatus as disclosed herein, can be utilized to provide sectioning capabilities and enhance the image contrast of superficial tissue microstructures and just as importantly, such identified structures can be stored and accessed in a desired data base. Such a data base enables the development of a library of analyzed tissue structures to further aid in the evaluation of conditions but more importantly to aid in the rapid assessment, diagnosis and recovery of patients.

Specific Description

Figure 1:
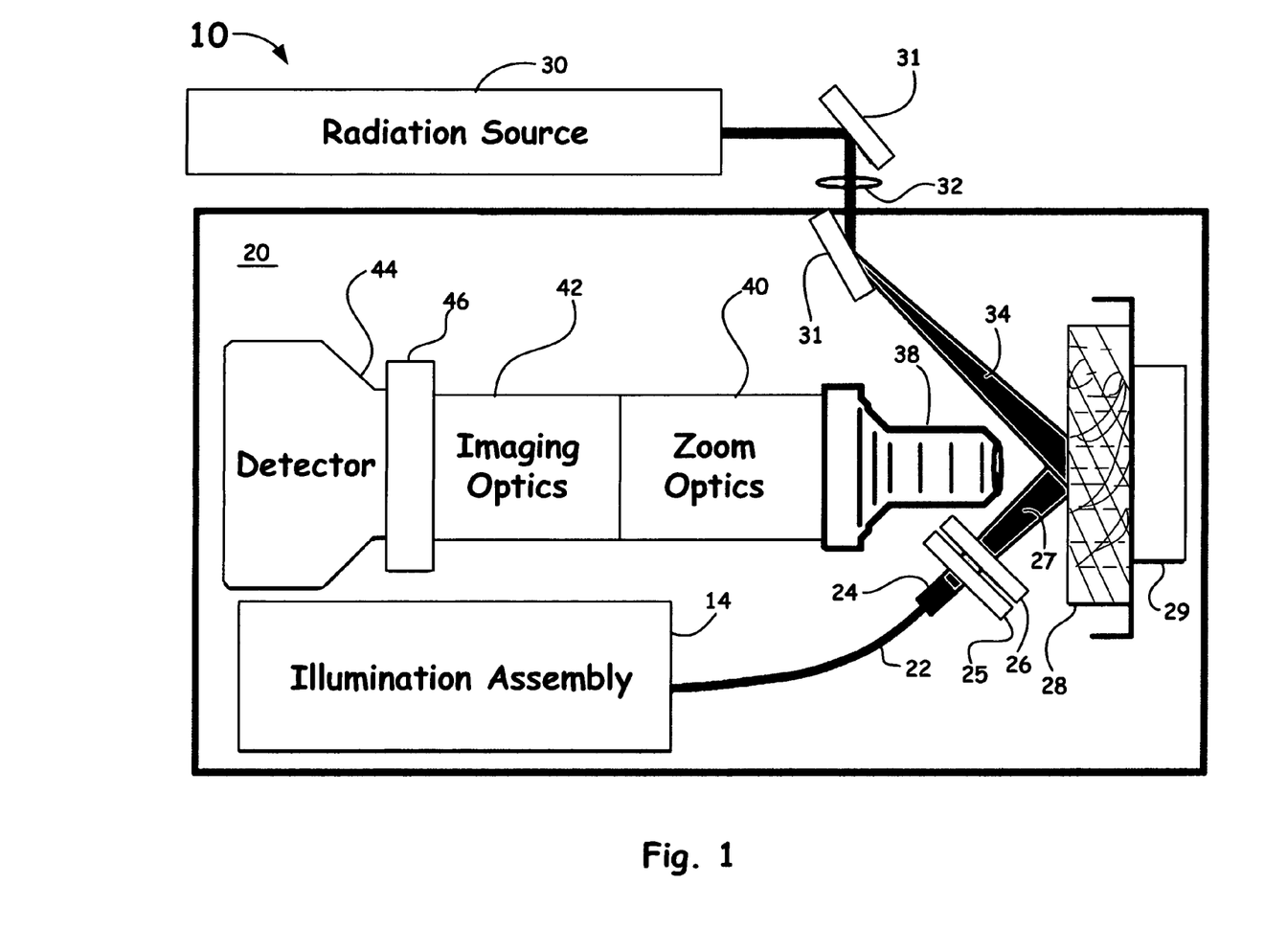
FIG. 1 shows a basic example schematic layout of a hyperspectral/multimodal microscope, designed for use in the laboratory for testing.

Turning now to the drawings, a diagram that illustrates an exemplary embodiment of a system constructed in accordance with the present invention is shown in FIG. 1. The system, designated generally by the reference numeral 10, and capable of being designed as a portable compact apparatus includes configured radiation sources, such as, broadband (e.g., white light) and/or continuous wave (CW) and/or pulsed coherent sources, (often having structured in intensity illumination and predetermined degrees of polarized outputs, e.g., linear, circular or elliptical polarization) arranged, for example, in an illumination assembly 14 or positioned as an external 16 radiation source outside of a major portable compartment 20. Such sources are configured to provide predetermined excitation wavelengths of at least 200 nm and if required, output optical energy in a pulsed format (e.g., one or more pulses in less than about 10 µsec in duration) to a targeted tissue component 17.

In a beneficial embodiment, a white light source (not shown) and predetermined coherent sources of the present invention, such as, Continuous Wave (CW) Helium-Cadmium and Helium-Neon lasers (not shown) and one or more compact diode-pumped solid state lasers (not shown) having beneficial excitation wavelengths of, for example, 266 nm, 325 nm, 355 nm, 408 nm, 532 nm and 632.8 nm are configured in illumination assembly 14. Illumination assembly 14 is further configured with optical means, such as, optical fibers and/or fiber bundles 22, and one or more appropriate optics known to one of ordinary skill in the art to enlarge (e.g., by using refractive optics 24), polarize (e.g., using linear, circular, and/or elliptical polarization filters 25), filter (e.g., using bandpass filters, narrow band filters, edge filters, etc. 26) and direct a predetermined illumination diameter(s) 27 so that an imaged area of a tissue sample 28 arranged on for example a sample stage, often a computer controlled X-Y-Z stage 29, can be exposed to the nearly uniform light intensity of the center portion of each directed beam.

An external radiation source 30, such as, but not limited to, an Optical Parametric Oscillator (OPO) (i.e., a nonlinear material capable of producing a coherent beam of light that can be tuned to operate at a predetermined wavelength over a wide range of wavelengths) along with the appropriate optics known to one of ordinary skill in the art, such as, for example, turning mirrors 31 and refractive optics 32 are also arranged to direct predetermined wavelengths of at least about 200 nm and produce a desired illumination diameter 34 having a predetermined intensity. Such a beneficial arrangement provides uniform light intensities of an exposed area to further enhance the autofluorescence and/or fluorescence capabilities of the present invention. A beneficially OPO embodiment of the present invention is a tunable wavelength system from 250 to 340-nm and 410 to 1000-nm upon optical pumping from a harmonically doubled Nd:YAG laser operating at 355 nm. While such coherent sources, such as the compact diode pumped solid-state lasers, the Continuous Wave (CW) Helium-Cadmium and Helium-Neon lasers, and the OPO discussed above are beneficial arrangements to be employed herein, any coherent continuous wave (CW) source and/or pulsed coherent source, more often a pulsed coherent source that can either generate one or more pulses of less than about 10 µsec in duration or be gated to produce a pulse like output of less than about 10 µsec in duration, and that can provide a wavelength(s) with sufficient intensity to enable monitoring of microstructures and cells in tissues may also be employed without departing from the scope and spirit of the present invention.

System 10 further includes an imaging system arranged in major portable compartment 20 that can include, but is not limited to, microscope objectives 38, magnification means 40, imaging optics 42, and detectors 44. The microscope objectives 38 as disclosed herein are designed to provide long working distances of between 3 mm and up to about 50 mm with large numerical apertures (e.g., an N.A. of at least about 0.3) for high light collection efficiency of a detected illumination so as to enable optimal spatial resolutions of down to about 0.5 µm. Optical information collected by a desired microscope objective 38 is then directed through optical magnification means 40, such as, for example, a zoom lens, and imaging optics 42 known to one of ordinary skill in the art to relay a desired image onto detector 44, such as, but not limited to, a spectrometer, a two-dimensional array detector, a multi-array detector, an on-chip amplification CCD camera, and a back-illuminated, liquid nitrogen cooled CCD detector or any equivalent means of digitized acquisition of one or more images.

In addition, an assembly holder 46 is often configured in the present invention to receive desirable polarizing optical components for polarization analyzing or discrimination experiments and/or predetermined optical filters for selected bands of wavelengths having predetermined narrow-band (e.g., 40 nm) spectral windows of up about the 1000-nm spectral range. While narrow-band interference filters can be employed in the present invention, any type of optical filtering means for the selection of a desired spectral window, such as, for example, broad spectral band filters or long-pass interference filters, can also be utilized for an imaging experiment without departing from the scope and spirit of the invention.

The output of detector 44 is capable of being characterized by a processor means (not shown), such as, but not limited to, a laptop computer or a personal computer configured with image processing software, and/or a human operator, such as, for example, a pathologist. The operator in using the present invention evaluates the microstructures and cells in tissues after being highlighted by the methods discussed herein and/or after inter-image processing by one or more visualization devices (e.g., computer monitor displays) so as to distinguish such microstructures and cells deemed important information to his or her trained eye.

The image quality of an in vivo microscope system, such as disclosed herein, depends not only on the designing characteristics of the optical components but also the degree to which the object being imaged can be kept immobilized with respect to the imaging system (microscope) during image acquisition. In vivo imaging is a problem due to intrinsic micro- and macro-movements of the vasculature, musculature, etc., tissue components. As another example arrangement, the present invention provides a novel solution to this problem by acquiring images much faster than the tissue can move beyond the instrument's specified spatial resolution of and relative to the imaging system. This can be achieved by using pulsed illumination such that the image is acquired from exposure to a single pulse. In such a case, the effective image acquisition time of, for example, an autofluorescence image, is on the order of a few nanoseconds (determined by the longer of the emission lifetime or laser pulselength). For example, using illumination of approximately 0.5 mJ/mm² in the UV obtained from a Q-switched laser, photoexcitation is sufficient to acquire a high quality image of the tissue. Even if the relative microscope-tissue speed of motion is an extreme value of 10 cm/sec, the relative movement during a 10 ns time interval is about 1 nanometer. Consequently, pulsed illumination less than about 10 µsec offers image acquisition fast enough to eliminate any loss in spatial resolution during in vivo application.

Since the imaging elements of the present invention are separated from the optical elements delivering the excitation light (via off-axis illumination) as shown in FIG. 1, excitation at one or more wavelengths is unrestricted by chromatic aberrations and the transmissive properties of optical components. This approach also eliminates any background signal (noise) arising from the optical elements, an issue most notable under UV excitation. Furthermore, off-axis illumination is capable of providing topological images of tissue, based on shadowing of the illumination light by microstructures in the tissue. This effect is maximized under UV excitation due to the smaller photon penetration depth.

Experimental Results

Figure 2A:
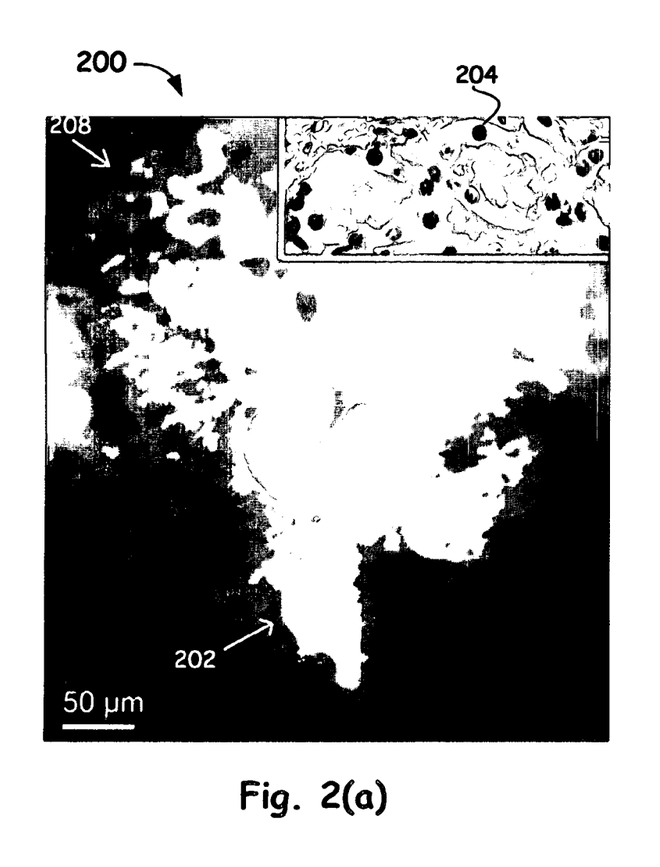
FIG. 2(a) shows a microscopic autofluorescence image of normal human kidney under 260-nm excitation. The inset in FIG. 2(a) illustrates a histologic structure of two kidney tubules from an Hematoxylin and eosin (H&E) stained section.

FIG. 2(a) shows an autofluorescence image of a cross section of a human kidney specimen, generally designated by the reference numeral 200, using a 10× objective with 260-nm excitation and 400-1000-nm (using a long pass filter) collection. The obtained specimen 200 is 4-mm thick and fresh from surgery without additional sample preparation. A plurality of normal tubules 202 is visible even to the untrained eye in the center of this image. Due to the limited depth of focus of the objective and the uneven surface of the sample, some of the features in this image are slightly out of focus.

Hematoxylin and eosin (H&E) is a differential stain found useful for studying histologic morphology in sections, wherein hematoxylin stains the nuclei of cells blue to bluish-purple and eosin stains other cellular elements in the tissues from pink to red. The inset in FIG. 2(a) illustrates the histological structure of the tubules 202 of the kidney from the image of an H&E stained section. Each tubule is composed of a single layer of cells. The nuclei of the cells appear as darker features 204 in the H&E stained section.

Figure 2B:
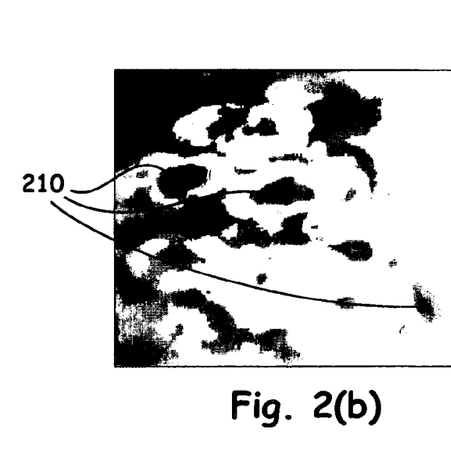
FIG. 2(b) shows an image of a set of sliced tubules by a surgical knife.

The features (as indicated by the denoted arrow 208) on the left side of the autofluorescence image shown in FIG. 2(a) are cross sections of the tubules cut by a surgical knife. FIG. 2(b) shows a close up image of such tubules near the location shown by the arrow 208 in FIG. 2(a). Thus, FIG. 2(b) shows a high resolution image of the sectioned tubules, indicating a thickness of the tubules at about 10-µm, equivalent to a single cell layer. The average pixel intensity of the digitized image of the approximately 10 µm thick body of the tubule is from about 40 to about 60% higher than the intensity in the middle of the tubule, providing contrast to visualize the tubular parenchyma microstructures. A careful examination of the cross section of the tubules reveals the presence of one or more darker features 210 that have the size and relative distance of the nuclei seen in the H&E stain of the inset as shown in FIG. 2(a).

Figure 2C:
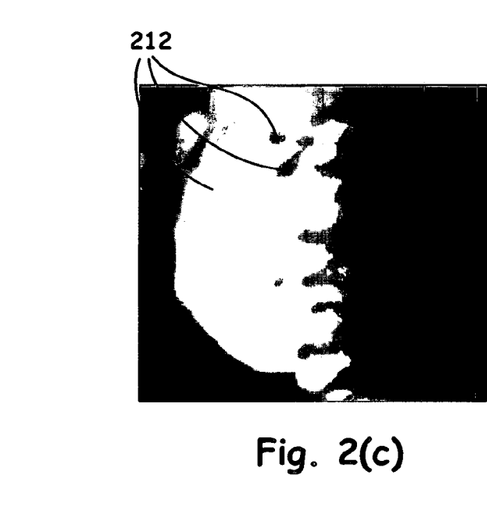
FIG. 2(c) shows an image of an intact tubule.

FIG. 2(c) shows an autofluorescence image under 260-nm excitation of the darker features 210 of FIG. 2(b) of an intact tubule (as taken from the area shown by the arrow in FIG. 2(a)). Autofluorescence under 260-nm excitation, such as the image shown in FIG. 2(c), arises predominantly from tryptophan emission. Such a higher resolution image of a single tubule clearly shows a plurality of darker features 212 (i.e., the features 210 as shown in FIG. 2(b), located 10 to 15-µm from each other. Such features 212 exhibit average intensities of about 20% lower than a surrounding area of a tubule's surface and are presumed to be the nuclei of the tubular cells.

Figure 3:
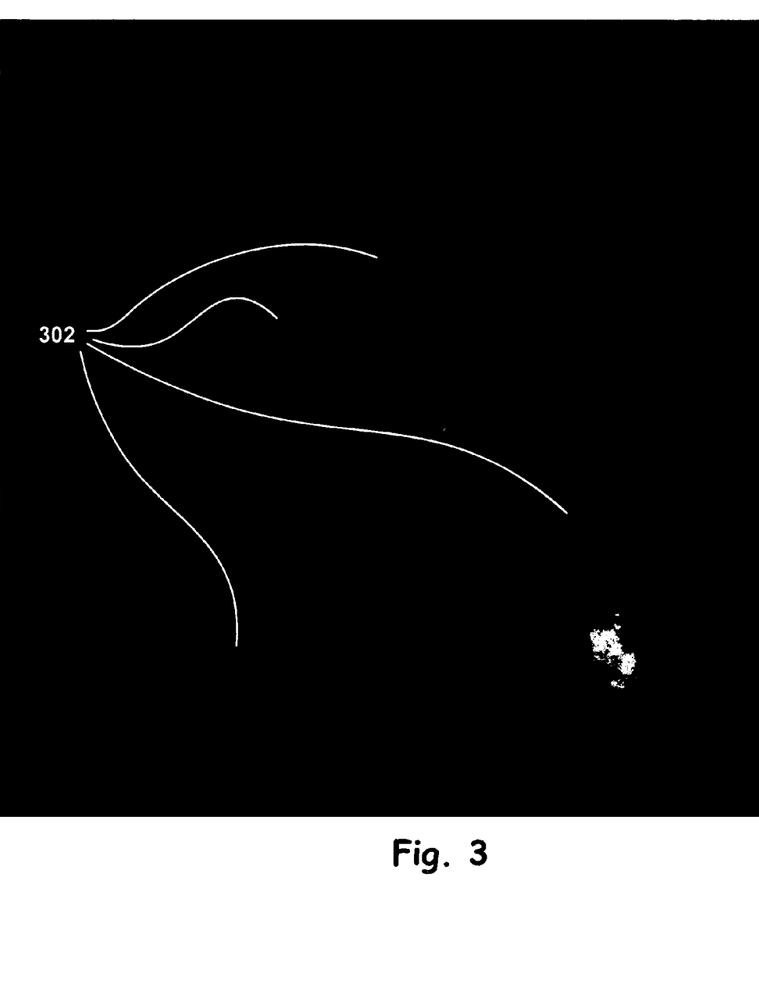
FIG. 3 shows a microscopic autofluorescence image of a 360×340 µm section of normal human kidney under 330-nm excitation.

FIG. 3 shows an image of a plurality of tubules 302, (i.e., similar to the tubules 202, as shown in FIG. 2(a)) from the same specimen under 330-nm excitation. The origin of the emission under this excitation is probably due to Nicotinamide adenine dinucleotide (NADH), a coenzyme that is present in all living cells. FIG. 3 demonstrates that the tubules are clearly visible under 330-nm excitation but the appearance of the tubules in this image is different compared to that under 260-nm excitation. More specifically, the darker features under 260-nm excitation as shown in FIGS. 2(a)-(c) (assumed to be the cells' nuclei) are not visible in FIG. 3 under 330-nm excitation. Instead, the emission intensity within the tubules is uneven and has features that exhibit higher intensity with diameters on the order of a few microns. Images using excitation wavelengths from about 250 nm to about 340 nm have also been recorded using the apparatus as shown in FIG. 1 and methods of the present invention. In general, images under 250 nm to about 280 nm excitation appear to be similar to those shown in FIG. 2. Images obtained under 300 nm to 340 nm excitation are similar to that shown in FIG. 3. Similar experiments have been performed using two more human kidneys obtained from experimental rats, as well as bovine and porcine kidneys obtained from the market with qualitatively the same results as discussed above.

NIR auto-fluorescence under long-wavelength excitation (green or red) offers contrast between normal and cancer tissue components depending on the type of tissue or organ as disclosed in incorporated by reference U.S. application Ser. No. 10/190,231. In the case of kidney cancer, the tumor appears as a darker feature compared to normal tissue. While such an imaging approach, which has been explored only in the macroscopic field is beneficial, the present invention improves on such techniques and apparatus by utilizing a simple high resolution imaging microscope and excitation illumination wavelengths of at least about 250 nm to provide auto-fluorescence induced by UV excitation in addition to NIR auto-fluorescence and other imaging modalities disclosed in the incorporated by reference U.S. application Ser. No. 10/190,231.

Figure 4A:
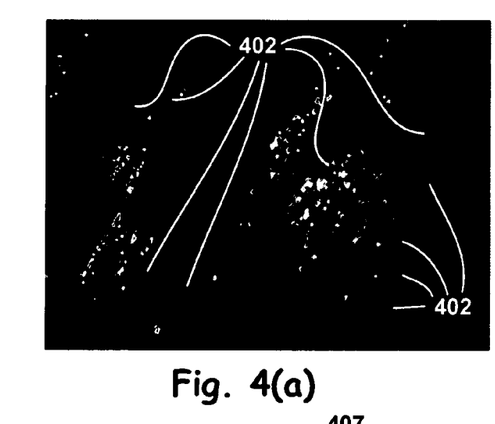
FIG. 4(a) shows a NIR autofluorescence image of a 960× 600 µm section of normal human kidney tissue under 532-nm excitation.

FIG. 4(a) shows an exemplary auto-fluorescence image of human kidney, generally designated by the reference numeral 400, using a 670-nm long pass filter and 533-nm excitation. The obtained specimen is 5-mm thick and fresh from surgery. A 1 second exposure time under 7-mW laser illumination is utilized to obtain the image as shown in FIG. 4(a). A plurality of tubules 402 (similar to the tubules 202, as shown in FIG. 2(a)) are clearly visible again due to autofluorescence. The bright features that contribute to the visualization of the tubules have intensities from about 20 to about 50% higher than the rest of the image.

Figure 4B:
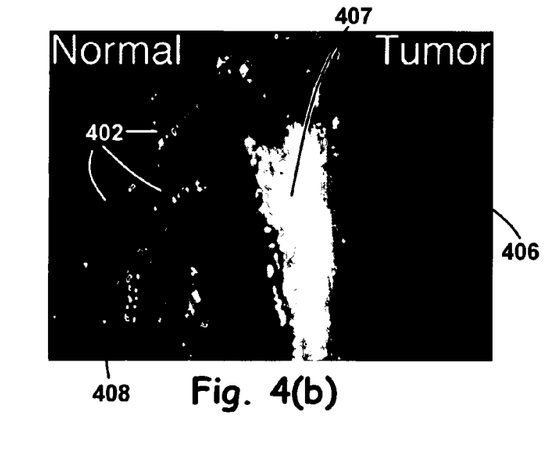
FIG. 4(b) shows a NIR autofluorescence image of a 960× 600 µm section of normal human kidney tissue under 532-nm excitation in the area of a tumor interface with the normal tissue.
Figure 4C:
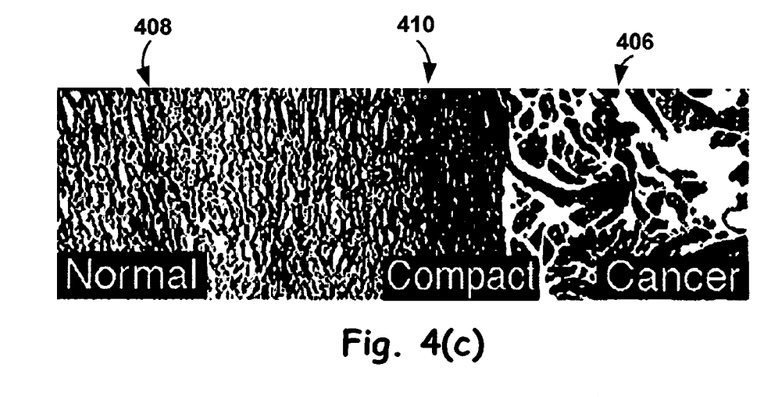
FIG. 4(c) shows a contrast enhanced H&E stains of the tumor-normal tissue interface.

FIG. 4(b) shows a NIR auto-fluorescence image of human kidney in an area where a tumor area 406 (papillary renal cell carcinoma) interfaces with a normal tissue area 408. The compression of the tubules 402 by the tumor at the interface is also clearly visible and appears as an area of enhanced emission 407 having about twice the intensity of the tumor area due to the compaction of the tissue and the tubules that are collapsing and respective enhancement of concentration of fluorophores. FIG. 4(c) shows a contrast enhanced H&E stained section of the same region, wherein the tumor area 406 (shown labeled as Cancer in FIG. 4(c)) is on the upper side, the lower side is the normal tissue area 408 (i.e., normal kidney parenchyma and shown labeled as Normal in FIG. 4(c)), and in the middle is a compacted normal tissue 410 (shown labeled as Compact in FIG. 4(c)) compressed by the expanding tumor 406.

Figure 4D:
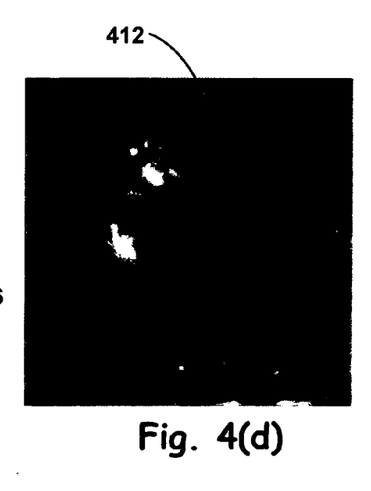
FIG. 4(d) shows a high magnification image of a normal kidney tissue.
Figure 4E:
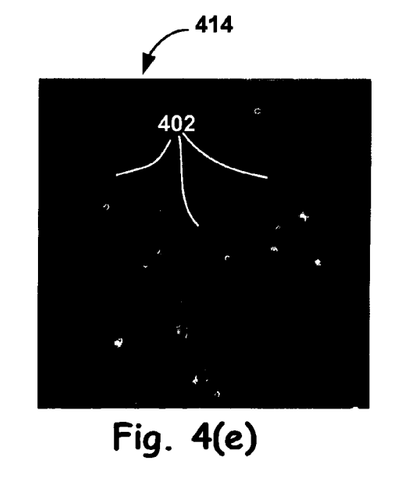
FIG. 4(e) shows a high magnification image of the tumor.

In the autofluorescence image of FIG. 4(b), the tumor 406 appears as a darker feature while the tubules 402 are brighter. A higher magnification image (110×140 μm) of a section from the tumor (i.e., tumor 406 as shown in FIG. 4(b)) is shown in FIG. 4(d). This image shows that the tumor has an irregular texture 412 with no organization. For comparison, an (190×220 μm) image from a normal kidney tissue area 414 having tubules 402 is shown in FIG. 4(e). The average intensity of the normal tissue area 414 in this image is about 18% higher than that of the tumor tissue 412, as shown in FIG. 4(d).

Figure 5:
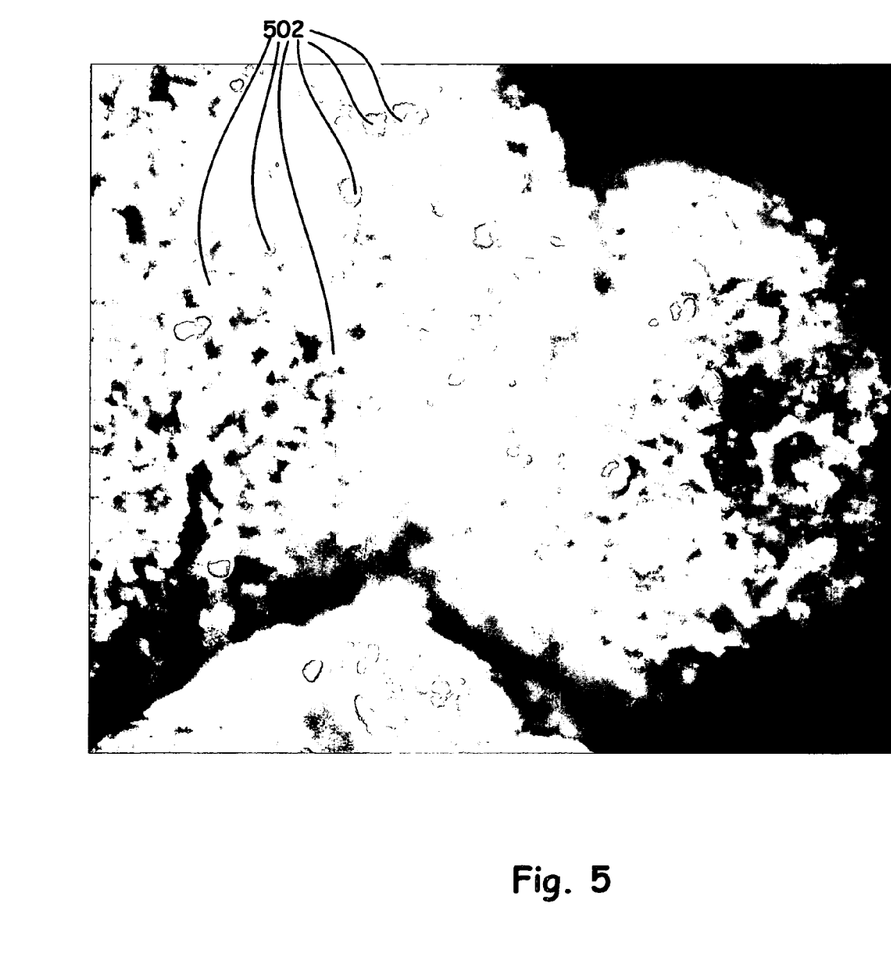
FIG. 5 shows an autofluorescence image of 650×500 µm section of the interior surface of porcine small intestine recorded under 280-nm excitation.

FIG. 5 shows an autofluorescence image of a 650×500-μm section from the inner surface of porcine small intestine recorded using a ×20 microscope objective and an excitation wavelength of 280-nm. A plurality of epithelial cells 502 are visible in the image of FIG. 5 and appear as round features with a diameter of about 10-μm. Best contrast using autofluorescence imaging of small intestine cells can be achieved using 280-nm excitation but the cells are also visible under all UV excitations as well as under about 408-nm illumination. Other tissues and organs such as liver, pancreas, colon and breast have also been investigated by the apparatus and methods of the present invention. In all cases, features can be directly related to the microstructure of given tissue.

While various tissue systems, such as, but not limited to, colon, liver, pancreas, bladder, esophagus, and normal tissue structures are beneficial structures to be imaged using UV illumination. A clear benefit in using UV excitation is that the short photon penetration depth due to absorption by tissue facilitates a low signal arising from the subsurface tissue layers providing for enhanced signal of the in-focus features on the surface layer of the tissue. On the other hand, imaging in the visible spectrum may offer valuable information to highlight disease specific optical signatures, such as that as shown in FIGS. 4(a)-(d). In these cases, imaging using UV excitation complemented by disease specific imaging in the visible or NIR may offer sufficient information for histopathologic evaluation and accurate delineation of a tumor's margins.

As another example embodiment of the present invention, relatively large structures (such as fat cells) can be imaged using light scattering. As an example, FIGS. 6(a)-(c) show light scattering microscopic images from a 850×1000 μm section of a human breast specimen obtained fresh following lumpectomy indicating an intersection between normal adipose tissue 602 (lower left) and a tumor tissue area 604 (infiltrating ductal carcinoma).

Figure 6A:
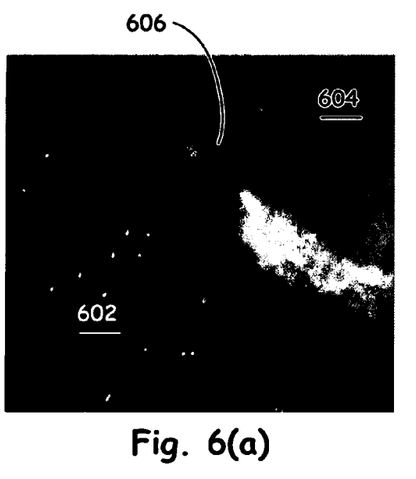
FIG. 6(a) shows a light scattering microscopic image of a 1000×850 µm section of a human breast specimen at the intersection of normal adipose and tumor tissue using an 450±20-nm filter.

FIG. 6(a) shows an unpolarized light scattering image of this specimen using white light illumination and a 450±20-nm narrow band filter in front of a detector of the present invention (CCD camera) having an exposure time of about 0.2 seconds. As can be seen in FIG. 6(a), the tissue components are distinctly different, permitting detection of a tumor edge 606 (margin) with high spatial resolution. The average image intensity of the normal tissue 602 is approximately 0.36 to that of the cancer tissue (tumor tissue area 604).

Figure 6B:
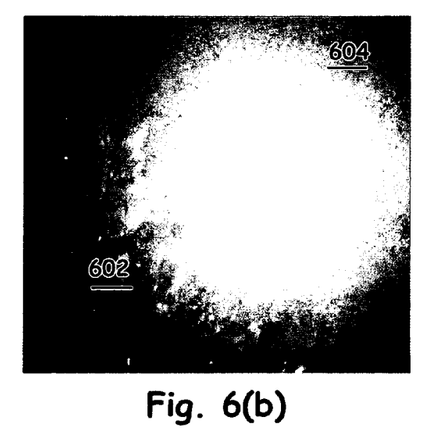
FIG. 6(b) shows a light scattering microscopic image of a same section of a human breast specimen at the intersection of normal adipose and tumor tissue using an 800±40-nm filter.

FIG. 6(b) shows an image of the same site under the same conditions but using an 800±40-nm filter for image formation. This image provides a lower contrast between normal adipose tissue 602 and cancer tissue (tumor tissue area 604). The average intensity in the image of the normal adipose tissue 602 measures to be approximately 0.88 to that of the cancer tissue (tumor tissue area 604).

Figure 6C:
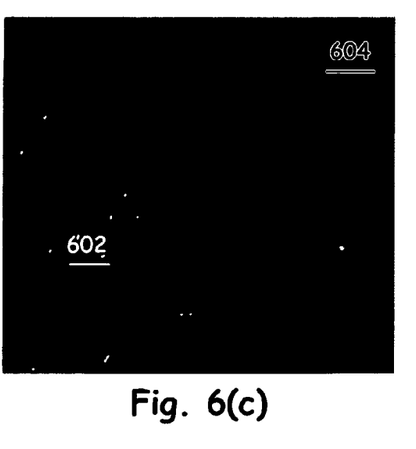
FIG. 6(c) shows a ratio image of light scattering microscopic images of the 1000×850 µm section of a human breast specimen, as shown in FIGS. 6(a) and 6(b), at the intersection of normal adipose and tumor tissue.

FIG. 6(c) shows a software processed image created by dividing, pixel by pixel, the light scattering image obtained under white light using a narrow band filter at 450±20-nm by the image obtained using an 800±40-nm filter. In this image, the contrast is further enhanced taking advantage of the spectral differences of the light scattering intensity from these tissue components.

Figure 6D:
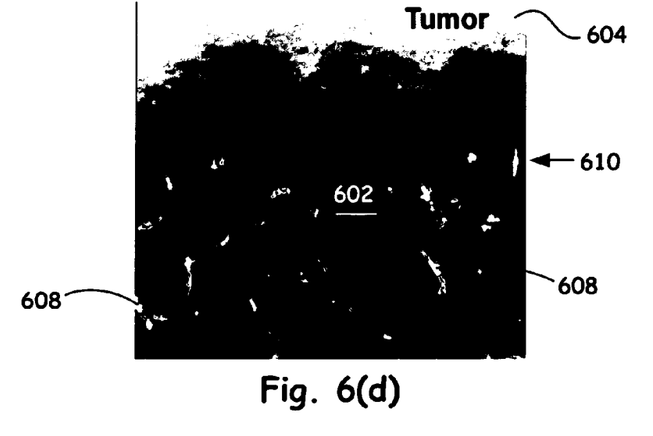
FIG. 6(d) shows a higher magnification ratio image of a 300×360 µm section.

The high spatial resolution in delineating the tumor's 604 margins is best depicted in FIG. 6(d), wherein a 360×300 μm section is shown at the intersection of the tumor tissue 604 with the normal tissue 602. The outline of a plurality of individual adipocytes (cells present in adipose tissue) is easily appreciated. Additionally, a first row 610 of normal adipose cells that are in contact with the tumor are clearly visible. The bright features in the normal tissue are consistent with the size and location of the nuclei of the adipose cells. In these images the tumor is clearly separated from the normal adipose tissue but the challenge is to separate cancer form normal connective tissue. In such a case, light scattering imaging and the utilization of autofluorescence imaging can be combined to address this issue.

Figure 7:
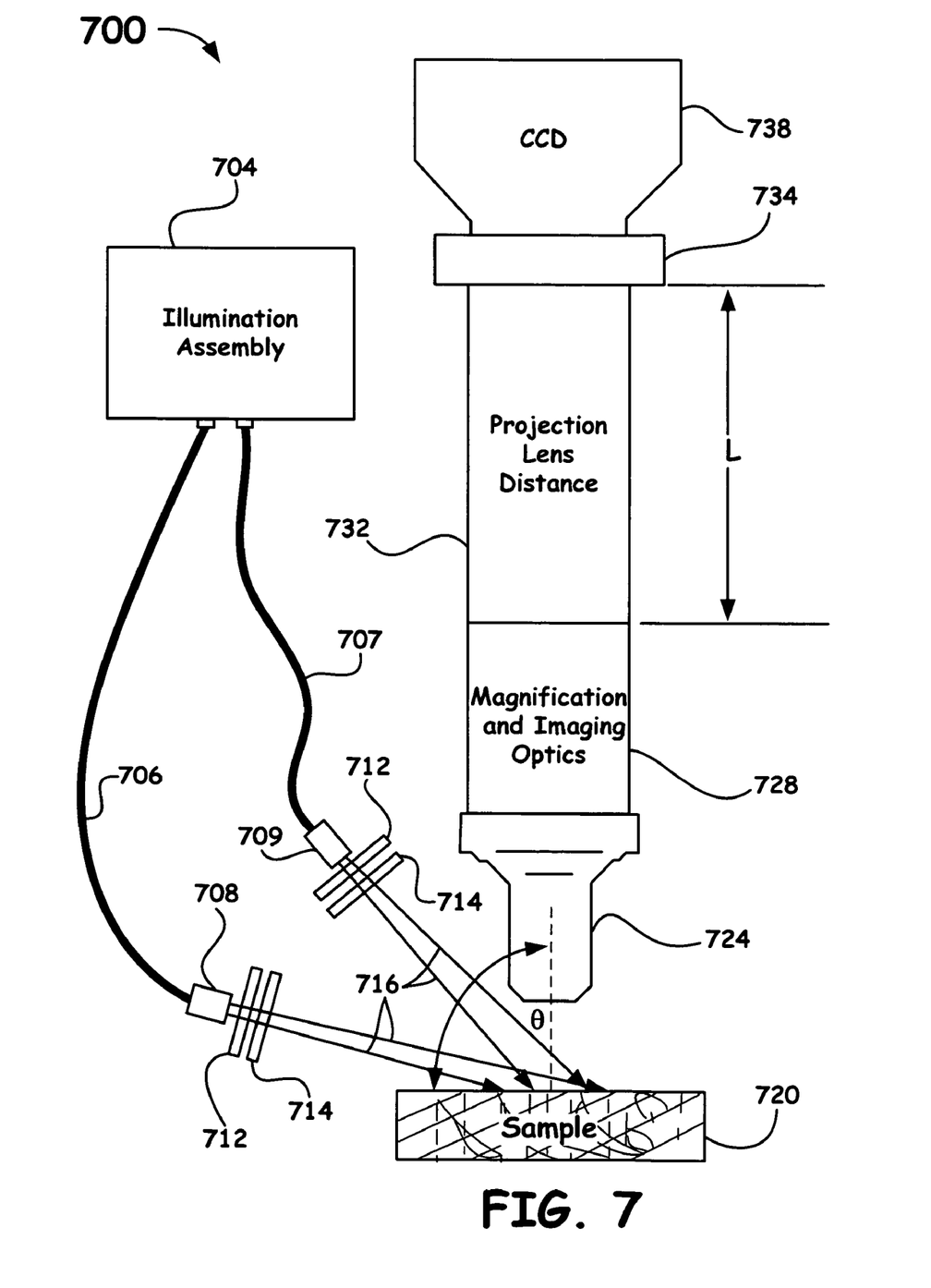
FIG. 7 illustrates another example arrangement of a hyperspectral/multimodal microscope of the present invention using, for example, off-axis illumination, one or more predetermined illumination wavelengths, at one or more predetermined angles of incidence.

Turning back to the apparatus embodiments, FIG. 7 illustrates a portable compact variation, designated generally by the reference numeral 700, of the exemplary embodiment of FIG. 1, as shown and discussed above. System 700, capable of being designed as a portable compact apparatus includes, for example, an illumination assembly 704 configured with one or more radiation sources (not shown), such as, broadband (e.g., white light) and/or (CW) or pulsed coherent sources, (often having structured in intensity and predetermined degrees of polarized outputs, e.g., linear, circular or elliptical polarization). Moreover, the radiation sources that can be arranged in the illumination assembly 704, can be designed to emit excitation wavelengths of at least 200 nm and similar to the arrangement shown in FIG. 1, provide one or more pulses of less than about 10 μsec in duration.

Configured with illumination assembly 704 is often one or more optical means, such as, optical fibers and/or fiber bundles 706 and 707, and one or more appropriate optics 708 and 709 known to one of ordinary skill in the art to enlarge (e.g., refractive optics) polarize (e.g., using linear, circular, and/or elliptical polarization filters 712), filter (e.g., using bandpass filters, narrow band filters, edge filters, etc. 714) and direct a predetermined illumination diameter(s) 716 so that an imaged area of a tissue sample 720 can be exposed to the nearly uniform light intensity of similar or different wavelengths (e.g., directing a different wavelength along optical fibers and/or fiber bundles 706 and 707) at substantially the center portion of each directed beam.

System 700 further includes an imaging system that can include, but is not limited to, microscope objectives 724, magnification means and imaging optics 728, a projection lens distance 732 defined by imaging properties of the optical components of the system 700, one or more processing optical components 734 (e.g., using linear, circular, and/or elliptical polarization filters, bandpass filters, narrow band filters, edge filters, etc.) and a predetermined detector 738, such as, but not limited to, a spectrometer, a two-dimensional array detector, a multi-array detector, an on-chip amplification CCD camera, and a back-illuminated, liquid nitrogen cooled CCD detector or any equivalent means of digitized acquisition of one or more images.

The microscope objectives 728 as disclosed herein are designed to provide long working distances of between 3 mm and up to about 50 mm with large numerical apertures (e.g., an N.A. of at least about 0.3) for high light collection efficiency of a detected illumination so as to enable optimal spatial resolutions of down to about 0.5 μm. detector 44

A novel aspect of the example arrangement, as shown in FIG. 7, is the capability of illuminating a predetermined tissue sample (e.g., 720) at one or more incident angles of up to about 90 degrees (as denoted by θ and as shown with the double arrow from sample 720 to the dashed line). More particularly, by directing predetermined CW and/or pulsed radiation at one or more angles via, for example, optical fibers and/or fiber bundles 706 and 707, and appropriate optics 708 and 709, the present invention can produce one or more images having, for example, different structural content of the tissues under investigation and can provide better image contrast in some cases with sectioning capabilities when processed by software. In addition, while such a two angle arrangement, as shown in FIG. 7, generally illustrates the capability of the present invention of directing predetermined radiation at various incident angles, the present invention can also provide rapid direction of predetermined radiation at various incidence angles via a variety of directing means, e.g., e-beam deposited beam-splitters, liquid crystal splitters, electro-optic devices, acousto-optic devices, mechanically driven reflective devices, and/or dichroic optics without departing from the spirit and scope of the present invention.

An additional novel aspect of the example arrangement, as shown in FIG. 7, is the implementation of a predetermined projection lens distance 732 that is provided by the focal lengths of the objectives 724 of the present invention. Specifically, by increasing the projection lens distance, and by providing pulses of less than about 10 μsec in duration upon illumination, out-of-focus photons are substantially not collected by the detection region of detector 738 (e.g., an imaging chip in a CCD), which improves the contrast of in-focus features of cells and tissues due to the rejection of such undesired out-of-focus photons photons. As an example arrangement, when configured with a projection lens distance 732 that can lead to system instabilities (i.e., due to mechanical constraints), optical directional means, such as for example, reflective and or refractive optics can be implemented in a fashion knoe to those of ordinary skill in the art to create an equal optical path length while physically being constrained to retain the compactness of the system of FIG. 7.

Figure 8A:
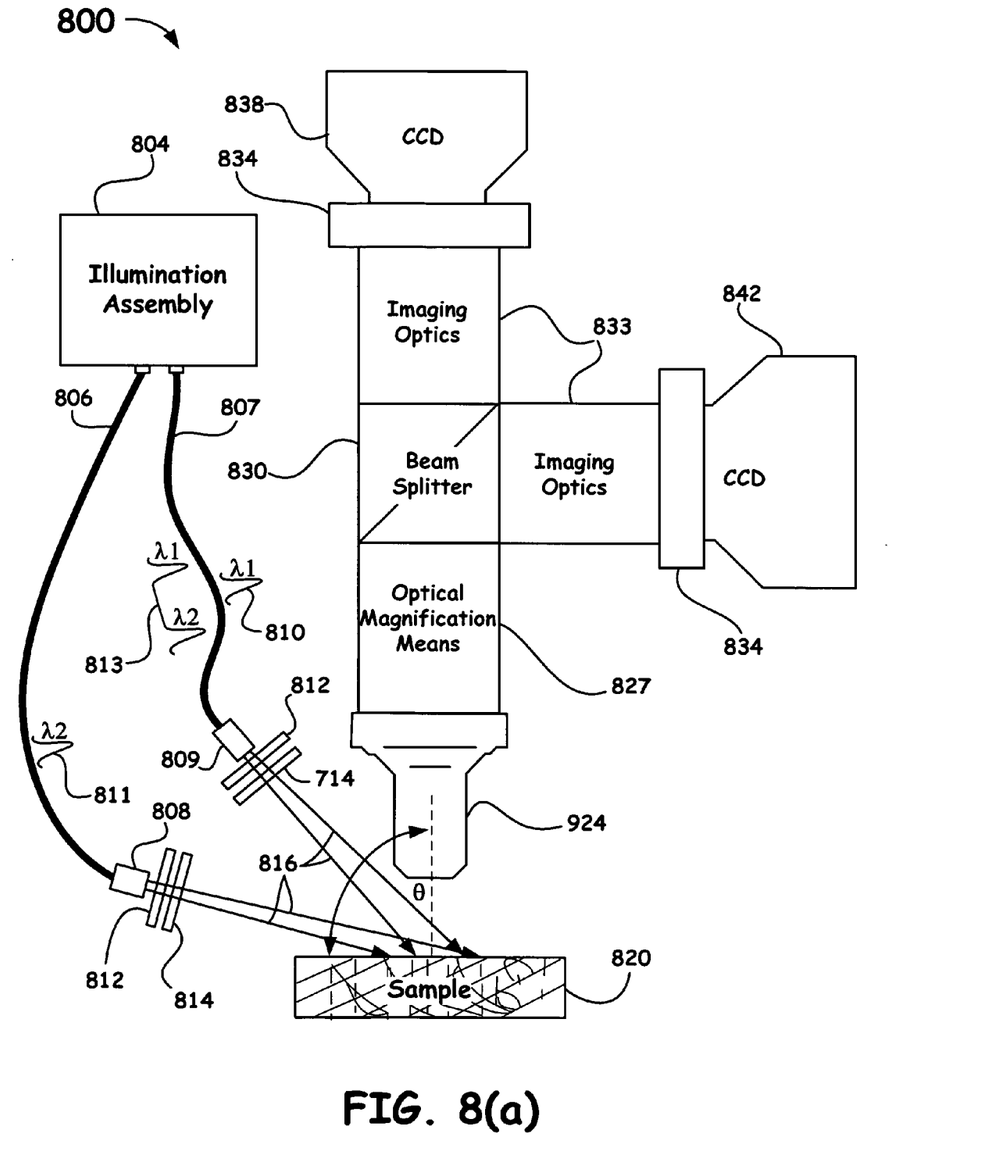
FIG. 8(a) illustrates another example arrangement of a hyperspectral/multimodal microscope of the present invention using, for example, off-axis illumination at one or more predetermined angles of incidence, one or more CCDs, different predetermined illumination wavelengths, and arranged to illuminate in a pulsed format.

FIG. 8(a) illustrates a variation of the portable compact configuration, as shown in FIG. 7, and is designated generally by the reference numeral 800. System 800, also capable of being designed as a portable compact apparatus includes, similar to that as shown in FIG. 7, an illumination assembly 804 configured with one or more radiation sources (not shown), such as, broadband (e.g., white light) and/or (CW) or pulsed coherent sources, (often having structured in intensity and predetermined degrees of polarized outputs, e.g., linear, circular or elliptical polarization). Again, the radiation sources can be arranged in illumination assembly 804 and adapted to emit excitation wavelengths of at least 200 nm in a CW or pulsed format (e.g., one or more pulses of less than about 10 μsec in duration).

Illumination assembly 804 can be arranged to provide one or more optical means, such as, optical fibers and/or fiber bundles 806 and 807, and one or more appropriate optics 808 and 809 known to one of ordinary skill in the art to enlarge (e.g., refractive optics) polarize (e.g., using linear, circular, and/or elliptical polarization filters 812), filter (e.g., using bandpass filters, narrow band filters, edge filters, etc. 814) and direct predetermined illumination diameter(s) 816 so that an imaged area of a tissue sample 820 can be exposed to the nearly uniform light intensity of similar or different wavelengths in a CW or in a pulsed mode format (e.g., one or more pulses of less than about 10 μsec in duration).

System 800 further includes an imaging system, similar but different to the configuration as shown in FIG. 7, that can include, but is not limited to, a microscope objective 824 as previously disclosed, an optical magnification means 827 (e.g., zoom lens), one or more optical beamsplitters 833 to direct predetermined collected emission, one or more processing optical components 834 (e.g., using linear, circular, and/or elliptical polarization filters, bandpass filters, narrow band filters, edge filters, etc.) and at least a pair of predetermined detectors 838 and 842, such as, but not limited to, a spectrometer, a two-dimensional array detector, a multi-array detector, an on-chip amplification CCD camera, and a back-illuminated, liquid nitrogen cooled CCD detector or any equivalent means of digitized acquisition of one or more images.

As an example illumination method of the invention in utilizing the configuration as shown in FIG. 8(a), one or more predetermined wavelengths (e.g., λ1) each having a desired pulsewidth (810) of less than about 10 μsec in duration can be directed at one or more predetermined incidence angles by, for example, optical fiber and/or fiber bundle 806 and one or more predetermined wavelengths (e.g., λ2) each having a desired pulsewidth and (811) of less than about 10 μsec in duration can also be sequentially directed at a predetermined incidence angle by, for example, optical fiber and/or fiber bundle 807 so as to illuminate substantially the center portion of a desired region of a tissue 820. High-resolution images are accordingly acquired during such pulsed illumination in time frames (e.g., less than about 10 μsec) much faster than a tissue can move beyond the system's specified spatial resolution, which is enabled by the pulse format protocols as disclosed herein. As another example method, one or more pulses, such as for example a pair of pulses 813 each having predetermined wavelengths λ1 and λ2 can be directed by a same optical means (e.g., optical fiber and/or fiber bundle 807) so as to provide spectral information of a given tissue 820 at different wavelengths λ1 and λ2 but now at a same predetermined incidence illumination angle. Once again, high-resolution images are acquired during such pulsed illumination in time frames (e.g., less than about 10 μsec) that is much faster than a tissue can move beyond the system's specified spatial resolution, which is enabled by the pulsed format of the present invention.

Figure 8B:
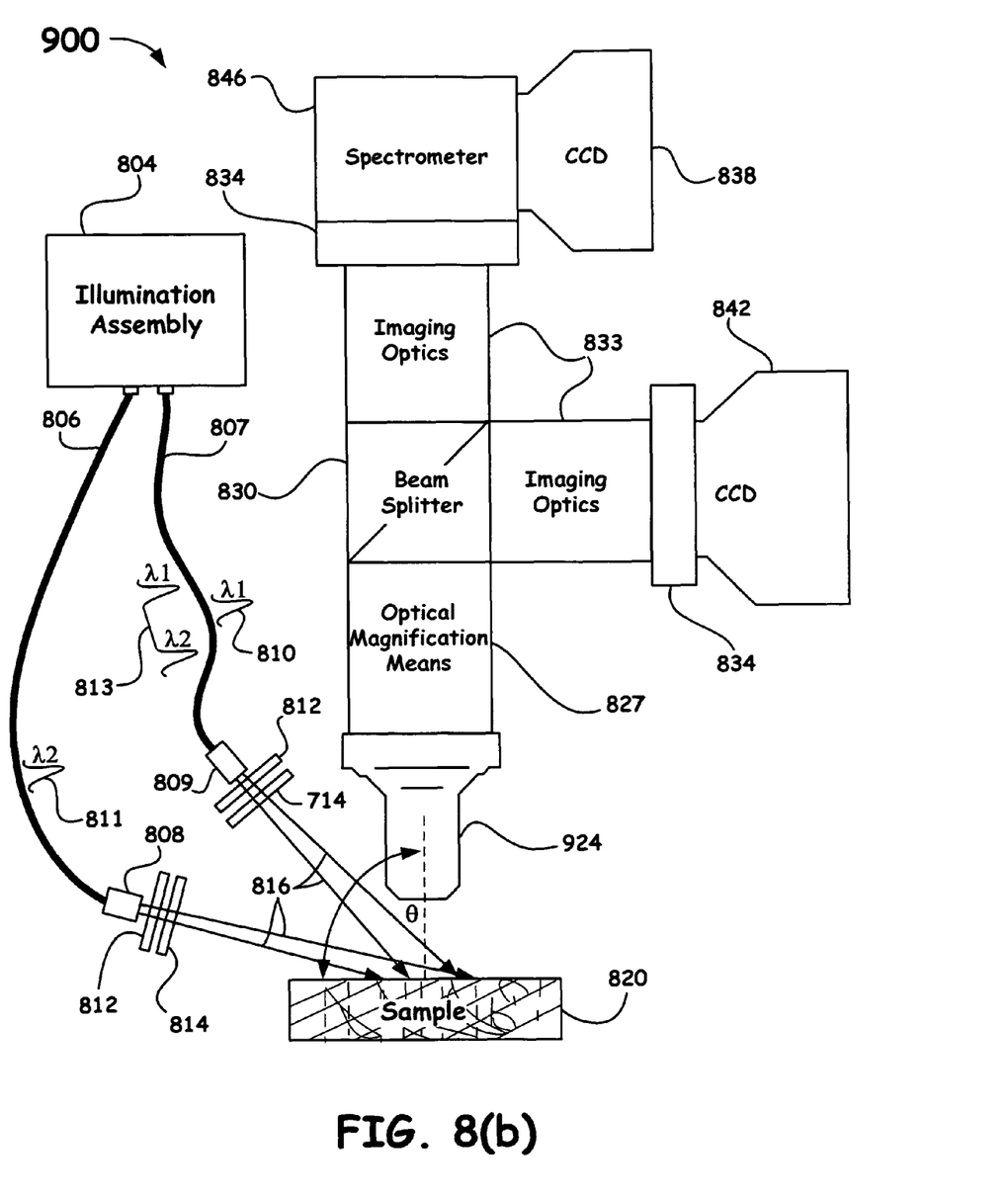
FIG. 8(b) illustrates the example arrangement of FIG. 8(a) with a spectrometer/CCD combination adapted as part of the detection apparatus and method.

FIG. 8(*b*) illustrates a variation of the portable compact configuration of FIG. 8(*a*), and is generally designated by the reference numeral 900. The modification of FIG. 8(*b*) with respect to the arrangement, as shown in FIG. 8(*a*) now includes a spectrometer 846 as part of the detection system to provide spectral line information that can be imaged by detector 838. All other reference characters are the same as utilized in the description and discussion regarding the arrangement of FIG. 8(*a*).

Figure 9:
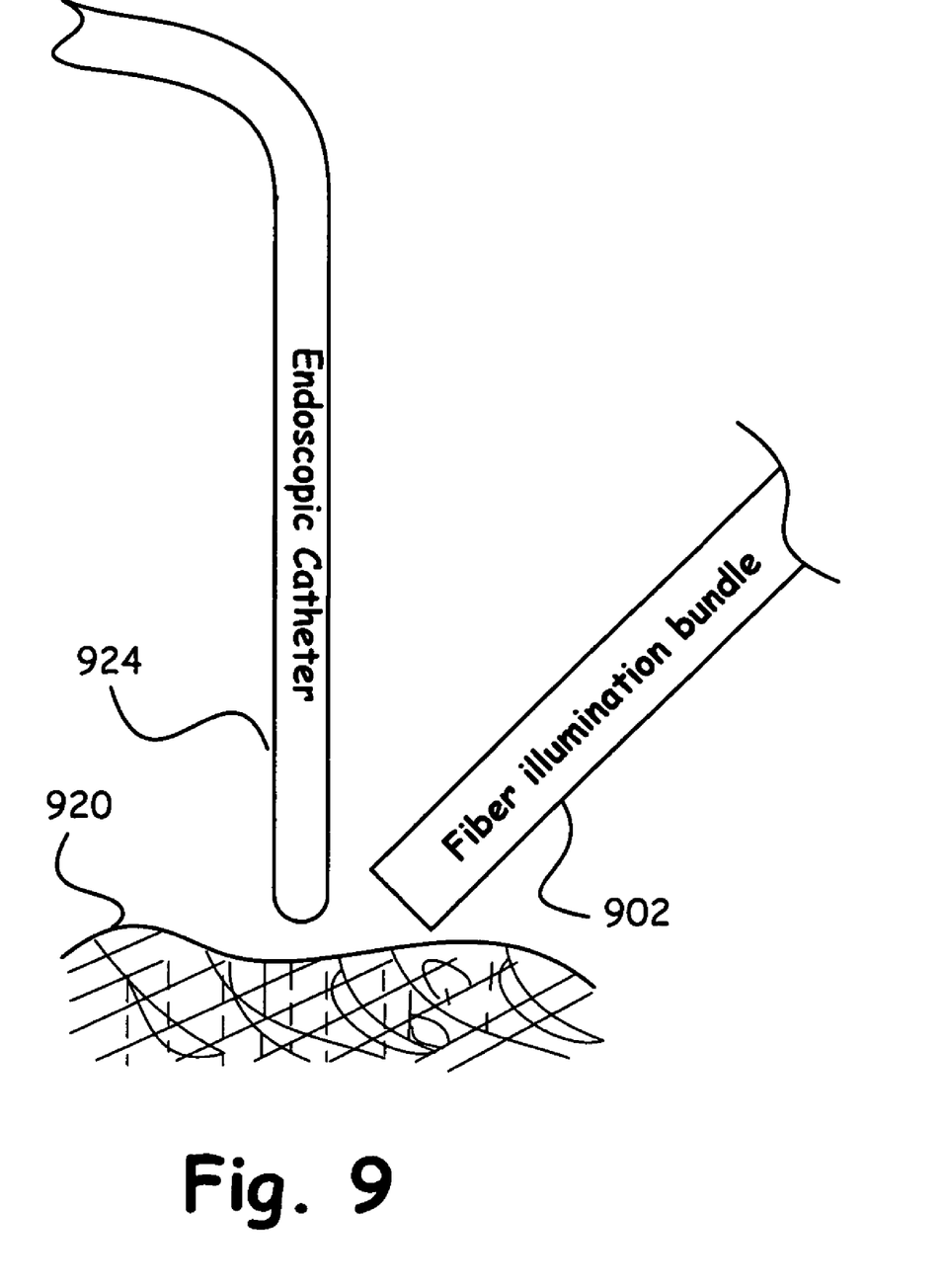
FIG. 9 shows a generic representation of a portable endoscopic, fiber-optic system of the present invention.

FIG. 9 illustrates generically an endoscopic example arrangement of the present invention wherein now CW and/or pulsed illumination is shown directed by a fiber illumination conduit 902 such as, an optical fiber bundle, to illumination in-vivo, a desired tissue region 920, and imaging takes place by optical components of the present invention that are arranged within, for example, within an endoscopic catheter 924. Such optical information is then processed after collection by detectors (not shown) disclosed herein and processed by methods as discussed above.

Accordingly, in a general method of the invention using a configuration, as shown in FIGS. 7, 8(*a*)-(*b*), and FIG. 9, cells and structures of tissue components can be interrogated and analyzed using the various spectroscopic techniques and imaging modalities disclosed herein (e.g., desired fluorescence, autofluorescence and/or scattered spectra of polarized and/or unpolarized light images). As part of the methods of the present invention, a plurality of high-resolution images can be collected in a given time frame (i.e., less than about 10 μsec) that is much faster than a tissue can move beyond the system's specified spatial resolution using the imaging system's discussed above, upon predetermined illumination wavelengths and pulse formats that are directed at predetermined incidence angles. Such a collection of images can then be image processed and manipulated via software (e.g., using inter-image operations) to further enhance contrast and visibility of selected tissue cells and structures while also assessing native tissue chromophores (e.g., NADH, Tryptophan, etc.) and/or exogenous fluorophores at the cellular and subcellular level in an expedient manner.

As stated above, but now with emphasis, applications of the high-resolution imaging instrument and methods disclosed herein include, but are not solely limited to, delineating a tumor's margins, screening of small tumors not visible in the macroscopic field, and monitoring of tissues or organs during treatment or exposure to adverse conditions (e.g., change of native tissue chromophore properties, location of uptake of contrast agent, cell swelling etc.). Additional applications include, but are not limited to, biosecurity, basic and applied research in Biology, injury ischemia recovery, dental tissue analysis, cosmetic tissue applications (e.g., nails, pigmentation or disease visualization), the detection and diagnosis of diseases (e.g., cancer), and the rapid pathological assessment and the capability of providing surgical guidance (e.g., civilian and battlefield trauma scenarios). It is to be appreciated that while a number of tissue components have been interrogated with the present invention, the invention is also beneficial in interrogating and assessing a host of other tissue components, such as, but not limited to, skin, nails, brain, and bone marrow tissue without departing from the scope of the invention.

Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The invention claimed is:

1. A high resolution optical imaging method, comprising:
    directing excitation light onto a target at an incidence angle to produce product light selected from the group consisting of a spectral band and a polarization state, wherein said target is selected from the group consisting of a tissue structure and a tissue cell, wherein said target has not been stained with contrast agent, wherein said excitation light comprises an ultraviolet wavelength within a range from 200 nm to about 355 nm;
    collecting, without a confocal microscope, said product light, using an optical element having microscopic resolution and an optical axis, wherein said incidence angle is off axis with respect to said optical axis, wherein said optical element comprises a long working distance objective, to produce collected target light; and
    processing said collected target light to produce an image comprising histopathology.

2. The method of claim 1, wherein the step of processing comprises producing images having a spatial resolution of about 0.5 μm or greater.

3. The method of claim 1, wherein said excitation light is produced by a continuous wave (CW) source.

4. The method of claim 1, wherein the step of directing excitation light includes directing pulses of excitation light at said target, wherein said pulses have a duration of less than about 10 μsec.

5. The method of claim 1, wherein said excitation light is at least one of polarized or structured in intensity.

6. The method of claim 1, wherein said collected target light is selected from the group consisting of scattered optical radiation and autofluorescence emission.

7. The method of claim 6, wherein said product light comprises a polarization component selected from the group consisting of a perpendicular-polarized component and a parallel-polarized component.

8. The method of claim 6, wherein said target light comprises emission from a native chromophore excited by said excitation light.

9. The method of claim 1, wherein the step of processing includes real-time in-vivo analysis of said structures and cells in said tissue components.

10. The method of claim 1, wherein the step of processing includes providing a data base of characterized tissue structures and cells.

11. The method of claim 1, wherein the step of processing includes inter-image manipulation after one or more images are collected at one or more predetermined incidence angles.

12. The method of claim 1, wherein said tissue components include at least one tissue selected from cancer tissue, stomach tissue, dental tissue, kidney tissue, colon tissue, breast tissue, skin tissue, nail tissue, brain tissue, pancreas tissue, bladder tissue, esophagus tissue, bone marrow tissue, intestine tissue, oral tissue, lung tissue, pancreas tissue and normal tissue.

13. The method of claim 1, wherein said long working distance objectives comprise one or more objectives having a numerical aperture (N.A.) of greater than about 0.3 to enable working distances of between 3 mm and up to about 50 mm.

14. The method of claim 1, wherein said one or more optical elements further comprise a predetermined projection lens distance so as to improve the contrast of in-focus features of said tissue components.

15. A hyperspectral/multimodal apparatus, comprising:
one or more optical radiation sources configured to provide excitation light to illuminate at one or more incidence angles the one or more structures and cells of predetermined tissue components, wherein said one or more structures and cells have not been stained with contrast agent, wherein said excitation light comprises an ultra-violet wavelength within a range from 200 nm to about 355 nm;
a non-confocal optical microscopic including long working distance optical elements, wherein said optical elements comprise an optical axis, wherein said optical elements are configured to collect one or more spectral bands and/or polarization states resulting from said structures and cells to produce collected one or more spectral bands and/or polarization states, wherein said one or more incidence angles are off axis with respect to said optical axis;
one or more detectors arranged to record said collected one or more spectral bands and/or polarization states; and
means for processing said collected one or more spectral bands and/or polarization states to produce an image comprising histopathology.

16. The apparatus of claim 15, wherein said apparatus comprises a spatial resolution of down to about 0.5 μm.

17. The apparatus of claim 15, wherein said long working optical elements enable off-axis illumination of said tissue components so as to substantially eliminate spectral noise resulting from one or more optical components.

18. The apparatus of claim 15, wherein said apparatus can be configured for real-time in-vivo analysis of said structures and cells in said tissue components.

19. The apparatus of claim 15, wherein said one or more detectors comprise at least one detector selected from the group consisting of a spectrometer, a two-dimensional array detector, a multi-array detector, an on-chip amplification CCD camera, and a back-illuminated, liquid nitrogen cooled CCD detector.

20. The apparatus of claim 15, wherein said means for processing comprise a computer having image processing software and means for displaying.

21. The apparatus of claim 15, wherein said one or more off-axis optical radiation sources comprise continuous wave (CW) sources.

22. The apparatus of claim 15, wherein said one or more off-axis optical radiation sources can be configured to comprise a polarized or structured in intensity output.

23. The apparatus of claim 15, wherein said collected one or more spectral bands and/or polarization states include bands and/or states selected from the group consisting of scattered optical radiation and autofluorescence emission.

24. The apparatus, of claim 23, wherein said autofluorescence emission comprises emission from a chromophore excited by said one or more off-axis optical radiation sources.

25. The apparatus of claim 15, wherein said polarization states comprise a polarization component selected from the group consisting of a perpendicular-polarized component and a parallel-polarized component.

26. The apparatus of claim 15, wherein said means for processing further comprises means for imaging said structures and cells resulting from ultra-violet (UV) excitation induced autofluorescence.

27. The apparatus of claim 15, wherein said means for processing comprise means for sectioning via imaging of said tissue components as a result of said one or more incidence angles.

28. The apparatus of claim 15, wherein said means for processing comprise a data base of characterized tissue structures and cells.

29. The apparatus of claim 15, wherein said means for processing comprise means for inter-image manipulation.

30. The apparatus of claim 15, wherein said tissue components are selected from the group consisting of cancer tissue, stomach tissue, dental tissue, kidney tissue, colon tissue, breast tissue, skin tissue, nail tissue, brain tissue, pancreas tissue, bladder tissue, esophagus tissue, bone marrow tissue, and normal tissue.

31. The apparatus of claim 15, wherein said apparatus is configured as a portable endoscopic system.

* * * * *